(12) United States Patent
Morgenshtein

(10) Patent No.: US 11,251,005 B2
(45) Date of Patent: Feb. 15, 2022

(54) METHODS AND SYSTEMS FOR USING A LIGHT EMITTING DIODE TO SWITCH A DEVICE ON AND OFF

(71) Applicant: GIVEN IMAGING LTD., Yoqneam (IL)

(72) Inventor: Arkadiy Morgenshtein, Haifa (IL)

(73) Assignee: GIVEN IMAGING LTD., Yoqneam (IL)

( * ) Notice: Subject to any disclaimer, the term of this patent is extended or adjusted under 35 U.S.C. 154(b) by 604 days.

(21) Appl. No.: 15/710,114

(22) Filed: Sep. 20, 2017

(65) Prior Publication Data

US 2018/0090290 A1 Mar. 29, 2018

Related U.S. Application Data

(60) Provisional application No. 62/399,671, filed on Sep. 26, 2016.

(51) Int. Cl.
*H01H 47/24* (2006.01)
*G01J 1/44* (2006.01)
(Continued)

(52) U.S. Cl.
CPC ......... *H01H 47/24* (2013.01); *A61B 1/00006* (2013.01); *A61B 1/00032* (2013.01); *A61B 1/00036* (2013.01); *A61B 1/041* (2013.01); *A61B 1/0684* (2013.01); *G01J 1/44* (2013.01); *G01J 1/0228* (2013.01); *G01J 1/4228* (2013.01); *G01J 2001/446* (2013.01)

(58) Field of Classification Search
CPC .. H01H 47/24; A61B 1/0006; A61B 1/00032; A61B 1/00036; A61B 1/041; A61B 1/0684
USPC .......................................................... 307/23
See application file for complete search history.

(56) References Cited

U.S. PATENT DOCUMENTS 7,850,006 B2 12/2010 Uchiyama
2007/0203414 A1* 8/2007 Axelrod ............... A61B 5/1459
600/478

(Continued)

OTHER PUBLICATIONS

Dietz et. al, "Very Low-Cost Sensing and Communication Using Bidirectional LEDs", Mitsubishi Electric Research Laboratories, 201 Broadway, Cambridge, Massachusetts 02139 USA, Jul. 2003, pp. 1-19.

*Primary Examiner* — Hal Kaplan
*Assistant Examiner* — Swarna N Chowdhuri
(74) *Attorney, Agent, or Firm* — Carter, DeLuca & Farrell LLP

(57) ABSTRACT

An on/off switching circuit includes an on/off switch switchable between an on state and an off state, an light emitting diode (LED) driver to power one or more LEDs to illuminate an area of interest, a switch control unit to transition the on/off switch between the on and off states, the switch control unit including a light sensing circuit comprising at least one LED of the LEDs as a light sensor, and a bi-directional gate circuit. When the on/off switch is in the off state the bi-directional gate is in a first conducting state in which the bi-directional gate circuit connects the light sensor to the light sensing circuit, and when the on/off switch is in the on state the bi-directional gate is in a second conducting state in which the bi-directional gate connects the LED driver to the one or more LEDs including the light sensor.

12 Claims, 5 Drawing Sheets

(51) Int. Cl.
*A61B 1/06* (2006.01)
*A61B 1/00* (2006.01)
*A61B 1/04* (2006.01)
*G01J 1/02* (2006.01)
*G01J 1/42* (2006.01)

(56) References Cited

U.S. PATENT DOCUMENTS

| | | | |
|---|---|---|---|
| 2007/0225560 A1* | 9/2007 | Avni | A61B 1/0684 600/118 |
| 2011/0125007 A1* | 5/2011 | Steinberg | A61B 1/041 600/424 |
| 2018/0039070 A1* | 2/2018 | Mao | F21V 5/007 |
| 2018/0217402 A1* | 8/2018 | Larmagnac | G02C 7/041 |

* cited by examiner

METHODS AND SYSTEMS FOR USING A LIGHT EMITTING DIODE TO SWITCH A DEVICE ON AND OFF

PRIOR APPLICATION DATA

The present application claims benefit from prior provisional patent application No. 62/399,671 entitled "METHODS AND SYSTEMS FOR USING A LIGHT EMITTING DIODE TO SWITCH A DEVICE ON AND OFF", filed on Sep. 26, 2016, incorporated by reference herein.

FIELD OF THE INVENTION

The present invention generally relates to switching circuits for switching systems "on" and "off", and more specifically to methods and systems for controlling the on/off state of an on/off power switch of systems, for example of in-vivo sensing capsules, of endoscopy capsules, and the like.

BACKGROUND

In-vivo imaging and measuring systems are known in the medical field, for example in what is commonly known as 'capsule endoscopy'. For example, some autonomous capsule like in-vivo devices, which traverse the gastrointestinal (GI) system, may include an imaging sensor, or imager, for imaging (e.g., capturing images or taking pictures of) the interior of the GI system. An in-vivo device may include sensors of other types (e.g., pH sensor, pressure sensor, temperature sensor, motion sensor, etc.), and/or various types of tools (e.g., micro electro-mechanical system, or "MEMS"), for example to perform surgical operations in vivo and/or to administer medication in the GI system, for example from a container contained in an in-vivo device.

Swallowable in-vivo devices may not accommodate a manually-operated on/off switch because such devices typically are air-tight and sealed and, in any case, they cannot be operated manually once swallowed. Nevertheless, quality control standards may require that each device be tested prior to use, which may require that the device be activated and deactivated, possibly several times, for testing purposes prior to use, and an in-vivo device must be switched "off" while not in use (in order not to preserve its battery's energy), and switched "on" just before it is swallowed.

Reed switches are commonly used, in some cases in conjunction with other devices or circuitry to activate and deactivate in-vivo devices prior to use. Being designed to be magnetically activated, reed switches are inherently sensitive to electromagnetic ("EM") fields, and may either be in "closed" state or in "open" state when exposed to an EM field. Some reed switches may be sensitive to mechanical shock that may have an unwanted effect on the devices they activate/deactivate, for example, during transfer and handling of the devices. Reed switches may unintentionally be activated by EM interference, for example by EM fields that may be used to maneuver the devices, or by random EM interference. In other cases, for example when the in-vivo device is not used for a long time, the electrical contacts of a reed switch may sometimes get stuck mechanically and, in such cases, it would not function reliably, or at all.

Alternatively, an on/off power switch may be controlled by using radio frequency ("RF") signals. Using RF signals to control the on/off state of a power switch may also have drawbacks. For example, such a switch may be prone to false activations/deactivations by RF interferences prior to use and during use (e.g., after it is swallowed). Another drawback of conventional switch control mechanisms is that they occupy space in the in-vivo devices, which impedes miniaturization of such devices. Another drawback of conventional switch control mechanisms is that they waste electrical power of the battery contained in the in-vivo devices.

While switching an in-vivo device, or other devices (e.g., implantable devices, miniature device, etc.) on and off is beneficial, there are some drawbacks associated with conventional on/off switching schemes, as specified above. It would, therefore, be beneficial to have an on/off switching scheme for such devices, which overcomes the drawbacks described above.

SUMMARY

While using an on/off switching mechanism is beneficial in activating and deactivating a device such as an implantable device or an in-vivo device, it would be beneficial to have an on/off switching mechanism that would operationally be more reliable, free up space in the device and allow the device to use a battery power more efficiently, for example during a medical procedure.

There is provided a swallowable in-vivo device that may include a battery, an imager including a pixel array, a light source (e.g., emitting diodes ("LEDs")), and a controller, where the controller may be configured to operate the imager and the light source in accordance with the methods described herein. The in-vivo device may include a battery, an image sensor, one or more LEDs, and a bi-directional gate (e.g., multiplexer (MUX)) to enable selective operation of the LEDs in two distinct operation modes: (1) a light source mode, to illuminate the GI tract, and (2) a light sensing mode, to facilitate activation (transitioning to an "on" state) and deactivation (transitioning to an "off" state) of the in-vivo device. While all, or some of, the LEDs of an in-vivo device may be used to illuminate the in-vivo device's field of view ("FOV"), a selected number or subset of LEDs may, at different times, be individually or collectively used as a light sensor to sense external light based on which the in-vivo device, or some of the functions it performs, may be activated (turned or switched on) or deactivated (turned or switched off).

In some embodiments, an on/off switching circuit may include an on/off switch switchable between an on state and an off state; an LED driver to, for example selectively, power one or more LEDs to illuminate an area of interest, and a switch control unit to transition the on/off switch between the on state and the off state. The switch control unit may include a light sensing circuit that may include at least one LED of the device's one or more LEDs that may form and function as a light sensor. The switch control unit may also include a light signal decoder to decode ('interpret') a light signal that is sensed by the LEDs serving as the light sensor.

The on/off switching circuit may also include a bi-directional gate circuit. The bi-directional gate is controllably switchable between a first conducting state and a second conducting state according to the decoded light signal, as described below. When the on/off switch is in the off state, the bi-directional gate may be in the first conducting state in which the bi-directional gate circuit electrically connects the light sensor to the light sensing circuit, and when the on/off switch is in the on state the bi-directional gate may be in the second conducting state in which the bi-directional gate electrically connects the LED driver to the one or more LEDs including the LED or LEDs of or forming the light sensor. The LED driver may include a DC/DC converter, to power the LEDs, and a current source for each LED, or for a group of LEDs.

In some embodiments, the bi-directional gate circuit may include one MUX. The MUX may electrically connect the LED, or LEDs, serving or used as the light sensor to the LED driver for illumination, or to the light sensing circuit in order for it, or them, to be used as the light sensor. In other embodiments, the bi-directional gate circuit may include two MUXs: a first MUX to connect (e.g. electrically connect) a first end of a LED serving as the light sensor either to a power supply (e.g., DC/DC converter) or to the light sensing circuit, and a second MUX to connect (e.g. electrically connect) a second end of the LED serving as the light sensor either to an electric current source or to a ground potential. A multiplexer may include a sensor LED selector ("SLS") to select a subset of the one or more LEDs for (to be used as) the light sensor. An in-vivo device may include the on/off switching circuit described herein.

BRIEF DESCRIPTION OF THE DRAWINGS

Various exemplary embodiments are illustrated in the accompanying figures with the intent that these examples not be restrictive. It will be appreciated that for simplicity and clarity of the illustration, elements shown in the figures referenced below are not necessarily drawn to scale. Also, where considered appropriate, reference numerals may be repeated among the figures to indicate like, corresponding or analogous elements. Of the accompanying figures.

DETAILED DESCRIPTION OF THE INVENTION

Figure 1:
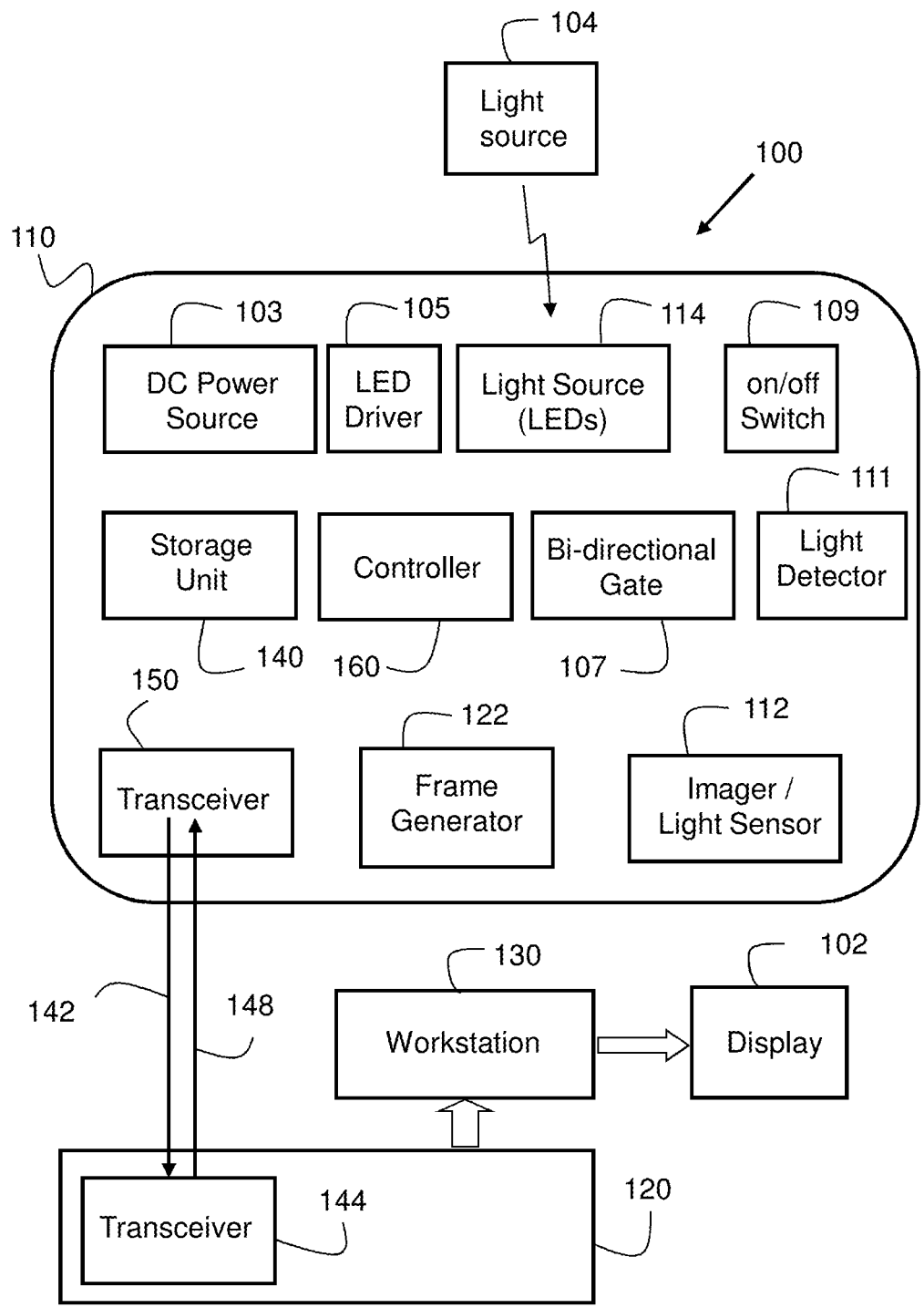
FIG. 1 shows a block diagram of an in-vivo device according to an example embodiment of the invention.

The description that follows provides various details of exemplary embodiments. However, this description is not intended to limit the scope of the claims but instead to explain various principles of the invention and the manner of practicing it.

In the following description, various aspects of the invention will be described. For purposes of explanation, specific configurations and details are set forth in order to provide a thorough understanding of the invention. However, it will also be apparent to one skilled in the art that the invention may be practiced without the specific details presented herein. Furthermore, well-known features may be omitted or simplified in order not to obscure the invention.

Conventional in-vivo imaging devices include a light source to illuminate the gastrointestinal ("GI") tract, and an imager to capture images of the GI. Typically, in-vivo imaging devices use LEDs as the light source because LEDs may have many advantages. In some embodiments LEDs (1) are tiny and relatively inexpensive; (2) are easy to control electronically; (3) last as a practical matter for certain applications forever, and (4) make light electronically without producing heat, which means that they save electrical energy. Since LEDs are already advantageously contained in in-vivo devices, it would be beneficial to use them not only to illuminate the GI tract, but also to change the on/off state of the power switch that activates and deactivates the in-vivo devices.

In-vivo devices transmit data (e.g., images, measurement information, etc.) to an external receiver using data frames (e.g., image frames), where each data frame may include data representative of, for example, an image captured in vivo by the in-vivo device, and, optionally, data representative of a physiological parameter (e.g., pH, pressure, temperature), or non-imaging parameters, that the in-vivo device may sense by using an on-board sensor. In-vivo imaging devices may operate according to a 'work cycle'. A "work cycle" may be a cycle or repeated time period or interval that includes an idle period during which the in-vivo device may capture an image and/or perform only internal tasks, and a transmission period during which the in-vivo device transmits a data frame (e.g., image frame), for example to an external receiver, via a communication channel.

The LEDs (or one LED) of the in-vivo device subject of some embodiments of the present invention may be selectively used in for example one of two operation modes: (1) a switch control mode (or light sensing mode), and (2) an illumination mode. In the control mode of operation the LEDs (or one LED) are(is) responsive to control light signal having predetermined characteristics that characterize an "on" command or an "off" command. Other numbers of modes may be used. The in-vivo device may transition (e.g. switch) from the "off" state to the "on" state if it senses (e.g. by using the LED(s)) a light whose characteristics indicate (the in-vivo device interprets it as) an "on" command. While the in-vivo device is in the "on" state, the in-vivo device may transition (e.g. switch) from the "on" state to the "off" state if it senses (by using the LED(s)) a light whose characteristics indicate (the in-vivo device interprets it as) an "off" command. When the in-vivo device is "on" (e.g., during normal operation of the in-vivo device), the LEDs may alternate between the illumination operation mode, in which the in-vivo device may capture images, and the control mode (or light sensing mode), in which the LEDs, or LED, are(is) put in a standby position, ready to sense light representing an "off" command. When the in-vivo device is "on", an external light signal corresponding to the "off" command may be turned on (e.g., emitted or radiated), for example, during a predetermined, or allocated, period in the in-vivo device's idle period. Examples of ways the in-vivo device subject of embodiments of the present invention is turned on and off by using a LED that is also used as a light sensor are described below in more detail.

FIG. 1 shows an in-vivo system 100 according to an example embodiment. The on/off state of in-vivo device 110 may be controlled optically by an external light source 104. In-vivo system 100 includes an in-vivo device 110 with an imager/light sensor 112 as an example light sensor. (Device 112, or part thereof, may be only an image sensor capable of capturing images, or only a light sensor, or it may perform both functions. In some embodiments, device 112 may be or include, for example, an array of pixels to capture images, or it may include one or more photodiodes.) Data frames transmitted by or from in-vivo device 110 may be referred to as "image frames" (although image frames may also include other types of data). In-vivo imaging system 100 also includes a data recorder 120 and a user workstation 130, which may be, for example, a personal computer, and a display 102 for displaying, for example, images and/or a video clip or moving image stream, or other data.

An in-vivo imaging device may have one or more imagers. By way of example, in-vivo imager 110 includes one imager (e.g., imager 112). In-vivo imager 110 may also include a light/illumination source 114 (e.g., LEDs) for illuminating a GI section to be imaged, a frame generator 122 for producing an image frame for each captured image, a controller 160, a storage unit 140 for storing data (e.g., images), a transmitter or transceiver 150 for transmitting (142) image frames and, optionally, for receiving (148) data and/or commands from data recorder 120. In-vivo imager 110 may also include an electrical power source 103 (e.g., a battery) for powering in-vivo device 110, and a LEDs driver 105. LEDs driver 105 may include a DC/DC converter or boost DC/DC.

At the time of, or shortly after, imaging device 110 is swallowed or otherwise inserted, or after some predetermined delay (e.g., 2 minutes), imager 112 may be switched on and start capturing images of areas of the GI system. Because natural light does not enter the intestinal tract, imager 112 does not require a light shutter, as opposed to 'regular' (i.e., non-swallowable) imagers. The function of the light shutter is, therefore, implemented by the darkness inside the intestinal tract and by intermittently illuminating the field of view ("FOV") of imager 112. Imager 112 may include an image sensor that may be, or include, an array of photo sensor elements (e.g., pixels) such as 256×256, 320× 320, 1 Mega pixel or any other suitable array. Imager 112 outputs image data by using a pixel format corresponding to the used pixels. Each image data may represent a captured image and, optionally, additional selected portions thereof.

Frames generator 122 may receive image data that represents a captured image, and produce a corresponding image frame (or "frame" for short) that contains the image data. A frame typically includes a header field that contains information and/or metadata related to the frame itself (e.g., information identifying the frame, the serial number of the frame, the time the frame, the bit-wise length of the frame, etc.), and a payload field. The payload may include an uncompressed version of the image data and/or a compressed version thereof, and a decimated image.

Controller 160 may controllably operate, among other things, illumination/light source 114 to illuminate areas traversed by in-vivo imager 110, and schedule the images capturing times accordingly. Controller 160 may use a timing unit to time the operation of illumination source 114 to illuminate, for example, four times per second to enable capturing four images per second, and the operation of transceiver 150 to concurrently transmit corresponding frames at the same rate or at a different rate. Controller 160 may use the timing unit to control LEDs driver 105, and, through LEDs driver 105, operate illumination source 114 to capture more images per second, for example seventeen images per second, and transceiver 150 to concurrently transmit corresponding frames at the same rate or at a different rate. Controller 160 may temporarily store captured images and related image frames in data storage unit 140. In some embodiments, one or more of the LEDs of light/illumination source 114 may be used both for illuminating imaged areas and for sensing light, for example sensing light emitted from light source 104.

Data recorder 120, which may be worn by the person whose GI system is to be imaged, may also include a receiver or transceiver 144, a frame parser (not shown in FIG. 9), and a processor for managing them. Data recorder 120 may include additional components (e.g., USB interface, Secure Digital ("SD") card driver/interface, controllers, etc.), elements or units for communicating with (e.g., transferring data frames, data, etc. to) a processing and/or displaying systems that may be configured to process images and localization data originating from in-vivo imager 110, and related data. Transceiver 144 may receive a data frame corresponding to a particular captured image, and the frame parser may parse the data frame to extract the various data contained therein (e.g., image data, decimated image associated with the particular captured image, etc.).

User workstation 130 may include a display or be functionally connected to one or more external displays, for example to display 102. Workstation 130 may receive frames (e.g., image frames, localization frames, etc.) or images from data recorder 120 and present them in real-time, for example as live video, or produce a video stream that also contains location and orientation information that may also be displayed on, for example, display 102. Workstation 130 may include a memory (not shown in FIG. 9) for storing the frames transferred from data recorder 120 and possibly related metadata, and a processor (not shown in FIG. 9) for processing the stored frames and related data. Workstation 130 may display selected images or a video clip (e.g., a moving image stream) compiled from such images, e.g., to a human operator, health care person, physician, etc.

When on/off switch 109 is in the "on" state (e.g., when the switch is "closed"), a bi-directional gate (e.g., MUX) 107 (a bi-directional path device that is always powered) connects (e.g. electrically or functionally connects) LEDs driver 105 (which, in the "on" state, is powered by DC power source 103) to LEDs 114 via a first path in bi-directional gate 107 to transfer power to LEDs 114. When switch 109 is in the "off" state (the switch is "open"), bi-directional gate 107 electrically disconnects the first path (to disconnect the LEDs from the power) and creates a second path (in a reversed direction) that electrically connects one or more LEDs of LEDs 114 to a light detector (light sensing circuit) 111, so that the LED(s) connected to light detector (light sensing circuit) 111 operate as a light sensor. Example electrical circuits that implement the LEDs control methods are shown in FIGS. 2-5, which are described below. Light sensing circuit 111 may also include a light signal decoder to decode light signals in order to determine (e.g., by controller 160) whether a detected light signal is a command to switch on/off switch 109 on or off. The light signal decoder may receive an output signal from the light sensor (e.g., from the at least one LED selected from the one or more LEDs) and control the on/off state of switch (circuit) 109 based on the light sensed by the light sensor.

Figure 2:
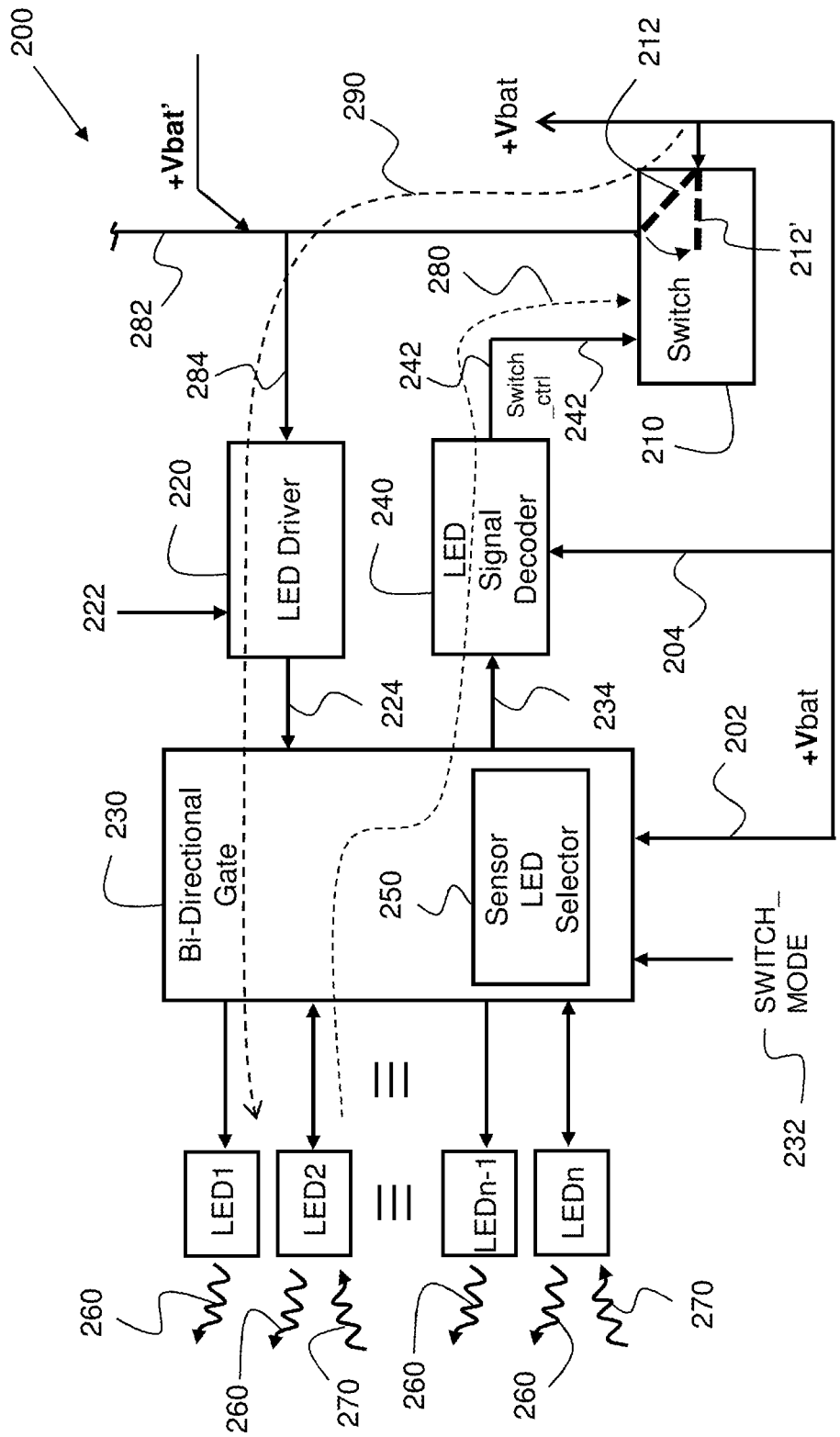
FIG. 2 is a block diagram schematically illustrating a general concept of a switch control scheme according to an example embodiment.

In some embodiments an in-vivo device (e.g., in-vivo device 110) may include one or more light emitting diodes (LEDs) and an on/off switching circuit identical or similar to on/off switching circuit 200 of FIG. 2). The on/off switching circuit may include a switch circuit identical or similar to switch circuit 210 (FIG. 2) that is switchable between an on state and an off state, an LED driver identical or similar to LED driver 220 (FIG. 2) to power the one or more light emitting diodes (LEDs), and a LED signal decoder identical or similar to LED signal decoder 240 (FIG. 2). The LED signal decoder may be configured to receive an output signal from a light sensor including at least one LED that may be selected from the device's one or more LEDs, and to control an on/off state of the switch circuit based on light that is sensed by the light sensor. The in-vivo device may also include a bi-directional gate identical or similar to bidirectional gate 230 (FIG. 2) that is switchable between a first conducting state in which the bi-directional gate circuit connects the light sensor to the LED signal decoder and a second conducting state in which the bi-directional gate connects the LED driver to the one or more LEDs including the LEDs functioning as the light sensor. Imaging device 110 may be switched on and off by the on/off switching circuit connecting (in the 'switched on' state) power source 103 to, or disconnecting it (in the 'switched off' state) from, selected electrical circuits of the imaging device. For example, in one embodiment an on/off switching circuit may control the power state (powered or disconnected from the power source) of all circuits in imaging device 110 except for the light sensing related electrical circuit which in one embodiment may be required to be powered at all times in order for it to be able to sense an on command even when imaging device 110 is in the off state. An on/off switching circuit according to embodiments of the present invention may switch on/off other components of a device.

FIG. 2 schematically illustrates a general concept of an on/off switching circuit 200 according to an example embodiment. On/off switching circuit 200 may include an on/off switch circuit 210 that includes a switch that is electrically connected, in one end, to a power supply (+Vbat) and, in the other end, to a LED driver 220. (Switch circuit 210 may include an on/off switch and an auxiliary electrical circuit that enables operating it.)

LED driver 220 may selectively power a set of LEDs, which may be selected from LEDs designated as LED1, LED2, ..., LEDn, via a bi-directional gate (e.g., multiplexer (MUX)) 230, when switch circuit 210 is in the on state. To that extent, LED driver 220 may include a same number of LED driver circuits, a LED driver circuit for each LED, or a LED driver circuit may drive a subgroup of LEDs. Bi-directional gate 230 may have two conduction states: one for connecting LED driver 220 to LEDs LED1-LEDn in order to selectively power these LEDs; another for connecting a light signal detector (a light signal interpreter or decoder; e.g., LED signal decoder ("LSD") 240) to one or more LEDs; e.g., LED2 and LED4, which may solely or additionally function as a light sensor. LED driver 220 may include a DC/DC converter to power the LEDs and, in addition, a separate electrical current source for each LED or for a group of LEDs.

LSD 240 may receive an output signal from the light sensor (e.g., from the at least one LED selected from the one or more LEDs for sensing light), and control the on/off state of switch (circuit) 109 based on the light sensed by the light sensor. LSD 240 may decode, or interpret, a light signal sensed by a subset of LEDs used as, or forming, the light sensor, which may controllably be selected from LEDs LED1, LED2, ..., LEDn by, for example, sensor LED selector (SLS) 250. (Interpreting, or decoding, a light signal sensed by a LED means identifying whether the light signal represents an "on" signal to transition switch circuit 210 from the off state to the on state, or an "off" signal to transition switch circuit 210 from the on state to the off state, or neither one of the two signals.) By way of example, the LEDs designate as LED1 and LEDn−1 are used only as a light source emitting light 260, and the LEDs designate as LED2 and LEDn are used as a light source emitting light 260 as well as a light sensor to detect light 270, with the two functions being facilitated by bi-directional gate 230.

SLS 250 may receive a command to select LEDs that will function as a light sensor according to a predetermined criteria. For example, if some LEDs are positioned in one side of the in-vivo device and other LEDs are positioned in another side of the in-vivo device, SLS 250 may receive a command to select LEDs (for sensing light) in a particular side of the in-vivo device, and such control may depend, for example, on the spatial orientation of the in-vivo device in the body accommodating it.

At least one LED of LEDs LED1 through LEDn may be used both as a light source to illuminate, for example, an imaged site, and as a light sensor to sense light indicating or representing an on command to switch on switch circuit 210 or an off command to switch off switch circuit 210. Bi-directional gate 230 and LSD 240 may be powered regardless of the state (off or on) of the switch circuit 210, as respectively shown at 202 and 204.

The conducting state of bi-directional gate 230 may be configurable by a control signal 232. When switch circuit 210 is in the off state, a light sensing path 280 applies, so control signal 232 (e.g. "SWITCH_MODE") controlling the conduction state (e.g. conduction 'direction') of bi-directional gate 230 may be set to a first logic state (e.g., "0") in order to cause bi-directional gate 230 to connect a light sensor, which may include one or more LEDs of LEDs L1 through LEDn, for example, LED2 (and possibly additional or other LEDs), to LSD 240 via connection path 234. (Assume that only LED2 is selected by SLS 250 as a light sensor. (Other or additional LEDs may be included in (e.g. selected for) the light sensor.) If LSD 240 identifies that the light sensed by LED2 represents an on signal, LSD 240 outputs a control signal 242 ("Switch_ctrl") that causes switch circuit 210 to transition to the on state. (The on state is shown in FIG. 2 as a 'bridge' 212 connecting battery voltage +Vbat to voltage supply line 282.)

Being connected (284) to voltage supply line 282 (in the switch's on state), LED driver 220 is powered and, therefore, operational, which means that LED driver 220 may drive LED1 through LEDn, or some of these LEDs, depending on an illumination control signal 222 that LED driver 220 may receive, for example, from a controller identical or similar to controller 160 of FIG. 1. (LED driver 220 may be configured to receive illumination control 222 signal indicating LED driver 220 to select specific LEDs of LEDs L1 through LEDn, or all of these LEDs, for illumination.) When the related in-vivo device is switched on by switch circuit 210, LED driver 220 may selectively power the LEDs at times (e.g., according to a predetermined schedule, or during a 'light' time window within the work cycle of the in-vivo device) in order to illuminate, for example, the GI tract. At other times, for example when no illumination is required, LED driver 220 may not power the LEDs.

When switch circuit 210 is in the on state, a LED driving path 290 applies, so control signal 232 (e.g. SWITCH_MODE), which controls the conduction state of bi-directional gate 230, may be set to a second logic state (e.g., "1") in order to cause bi-directional gate 230 to connect LED driver 220 to LED1-LEDn via connection path 224, so that LEDs LED1 through LEDn (or a subset of these LEDs) may be conditionally (depending on illumination control signal 222) activated (powered to illuminate).

As described herein, when the in-vivo device is switched on, it may be that the LEDs LED1-LEDn need not be active (may not need to illuminate). During such 'light' inactive periods, control signal 232 (e.g. SWITCH_MODE) controlling the conduction state (direction) of bi-directional gate 230 may return to the first logic state (e.g., "0") that causes bi-directional gate 230 to connect (re)connect the light source (e.g., LED2) to LSD 240 via connection path 234. If LSD 240 identifies that a light sensed by LED2 represents an off signal, LSD 240 outputs a control signal 242 (Switch_c- trl) that causes switch circuit 210 to transition to the off state. (The switch's off state is shown as bridge 212 at position 212' in which battery voltage +Vbat is disconnected from voltage supply line 282.) Being disconnected from the voltage supply +Vbat, LED driver 220 is deactivated.

In some embodiments, on/off switching circuit 200 may include a switch circuit 210 that is switchable between an on state and an off state, an LED driver 220 to selectively power one or more light emitting diodes (LEDs), and a switch control unit to operate switch circuit 210. The switch control unit may include a light sensing circuit and a light signal decoder (e.g., LED decoder 240). The light sensing circuit may include at least one LED (e.g., two LEDs; e.g., LEDs LED2 and LED4) of the device's one or more LEDs that may form, and function as, a light sensor. The light signal decoder may decode (interpret) a light signal that is sensed by the light sensor. On/off switching circuit 200 may also include a bi-directional gate 230 to connect LEDs of LEDs LED1-LEDn to LEDs driver 220, to power these LEDs, while switch circuit 210 is in the on state, or to connect the LEDs functioning also as the light sensor to light decoder 240, to sense light signals, when switch circuit 210 is in the off state. Bi-directional gate 230 may be controlled (e.g., by a controller controlling the state of SWITH_MODE input 232) to reconnect the LEDs functioning as the light sensor to light decoder 240, for example periodically or aperiodically, when switch circuit 210 is in the on state but there is no need to operate the LEDs as a light source; that is, when there is no need for illumination.

Figures 3A, 3B:
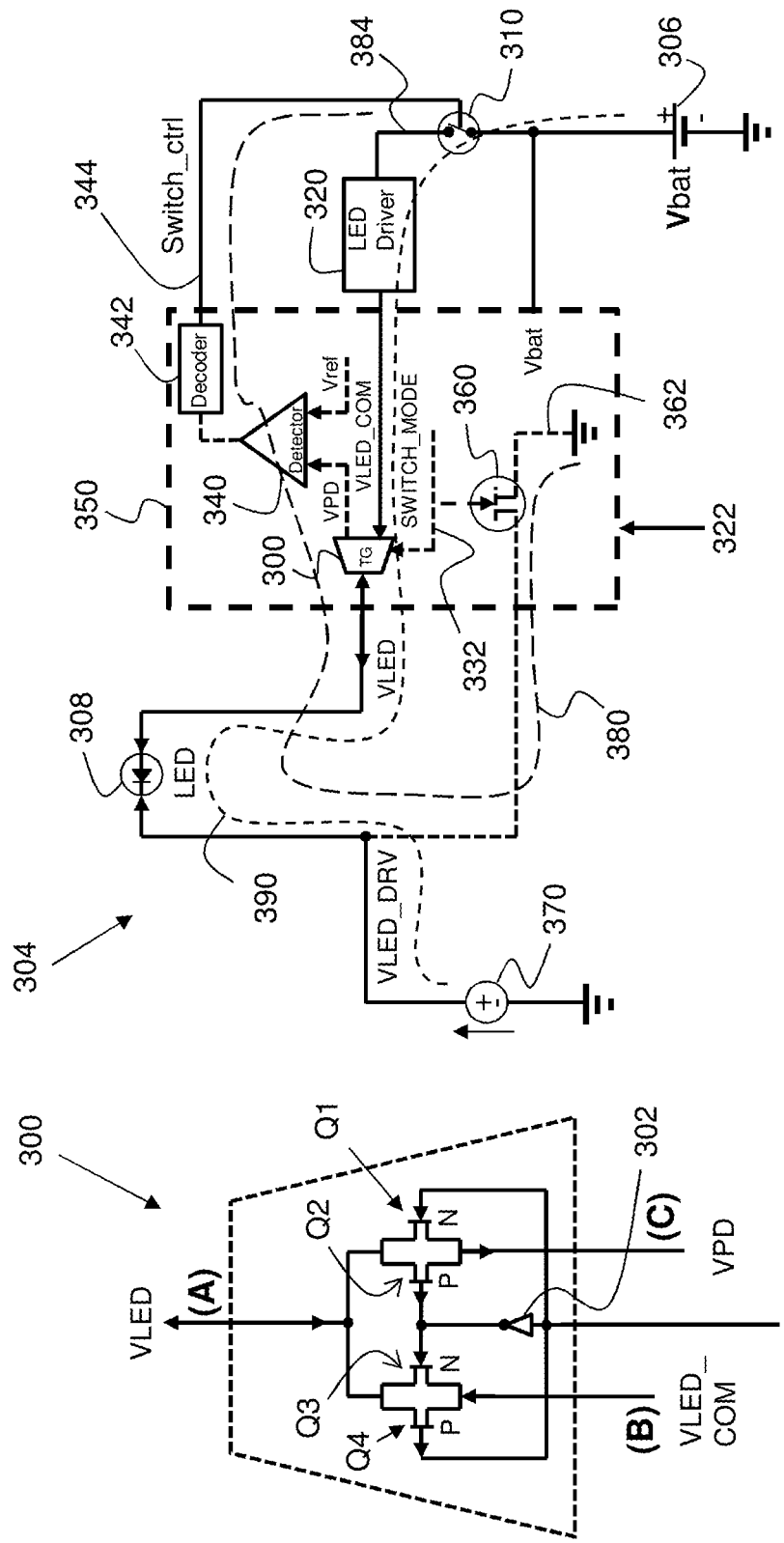
FIG. 3A shows a bi-directional gate useful for controlling the on/off state of a switch according to an embodiment of the invention.
FIG. 3B shows an electrical circuit according to an example embodiment.

FIG. 3A schematically illustrates a bi-directional gate (e.g., MUX) 300 according to an example embodiment. Bi-directional gate 300 may include four transistors (e.g., junction gate field-effect transistor "JFET" transistors), designated as Q1, Q2, Q3 and Q4. Transistors Q1 and Q3 may be N-channel JFET transistors, and transistors Q2 and Q4 may be P-channel JFET transistors. Conjugated transistors Q1 and Q2 make up a first unidirectional 'gate' to pass signal VLED from side (A) to side (C) of bi-directional gate 300. Conjugated transistors Q3 and Q4 make up a second unidirectional gate that can pass signal VLED_COM from side (B) to side (A) of bi-directional gate 300.

Each of four transistors Q1-Q4 includes a control gate (G) that enables transitioning them between, for example, a fully conductive ("saturated") state (low impedance between the respective D and S terminals) and a fully cut-off (high impedance between these terminals).

Bi-directional gate 300 may include a logic inverter (logic NOT gate) 302 to convert the logic state of a control signal SWITCH_MODE. When the MUX's control signal SWITCH_MODE is at logic state one (when SWITCH_MODE="1", $\overline{\text{SWITCH\_MODE}}$="0"), transistor Q1 fully inducts thanks to signal SWITCH_MODE (Q1 is an N-channel JFET transistor), transistor Q2 fully inducts thanks to signal $\overline{\text{SWITCH\_MODE}}$ (Q2 is a P-channel JFET transistor), transistor Q3 is cut off thanks to signal $\overline{\text{SWITCH\_MODE}}$ (Q3 is a N-channel JFET transistor), and transistor Q4 is also cut off thanks to signal SWITCH_MODE (Q4 is a P-channel JFET transistor). Namely, when SWITCH_MODE="1", transistors pair Q1 and Q2 simultaneously open a conductive path in direction (A) to (C) while transistors Q3 and Q4 are cut off (electrically disconnected). Conversely, when SWITCH_MODE="0", transistors pair Q3 and Q4 simultaneously open a conductive path in direction (B) to (A) while transistors Q1 and Q2 are cut off (electrically disconnected).

By determining the logic value, or control value in general, of the control signal SWITCH_MODE (e.g., by a controller; e.g., controller 160 of FIG. 1), bi-directional gate 300 can be used to transfer, in one direction, power (e.g., from a LED driver; e.g., from LED driver 220 of FIG. 2) to LEDs for illumination, or to transfer, in the opposite direction, a signal representing sensed light from a LED serving as a light sensor to a light detector; e.g., LED signal detector 240.

FIG. 3B schematically illustrates an optical switch circuit 304 that uses bi-directional gate 300 according to an example embodiment. Optical switch circuit 304 may include an on/off switch circuit 310 that is connected, in one end, to a power supply 306 (+Vbat) and, in the other end, to a LED driver 320. (Switch circuit 310 may include an on/off switch and an electrical circuit for operating it.) LED driver 320 may power a set of LEDs, though only one LED is shown (LED 308), via bi-directional gate 300, when switch 310 is in the on state. Optical switch circuit 304 may also include a light detector 340 to detect light that is sensed by LED 308 when it serves as a light sensor. LSD 342 may receive the output signal of light detector 340, which is a function of the light sensed by LED 308, and decode (interpret) the decode it as an on command, or as an off command, or as neither command. Light detector 340 and LSD 342 may collectively be referred to as LSD 342'. LED 308 may be used as a light source as well as a light sensor, with the two functions being facilitated by bi-directional gate 300.

Bi-directional gate 300 and LSD 342' of circuit 350 may be powered regardless of the state of the switch circuit 310. When switch circuit 310 is in the off state, a light sensing path 380 applies, so a control signal 332 (e.g. "SWITCH_MODE") controlling the conduction state (e.g. direction) of bi-directional gate 300 is set to a first logic state (e.g., "0") causing bi-directional gate 300 to connect LED 308 to LSD 340. Control signal 332 (e.g. SWITCH_MODE) also transitions a transistor 360 into the conducting state to thus provide a ground potential 362 to LED 308 while LED 308 is in the light sensing mode of operation in which LED 308 is operated as a light sensor. (To use a LED as a light sensor, one of its two terminals is to be connected to a reference potential (e.g., ground) while the other terminal outputs an electrical signal that represents a light that the LED senses. Transistor 360, by functioning as an auxiliary switch, connects and disconnects ground potential 362, or another reference voltage, to, or from LED 308 according to (e.g. in synchronization with) the logical value of the switch control signal SWITCH_MODE 332.)

One input terminal of LSD 340 is connected to a reference voltage (Vref), and another terminal of LSD 340 receives, via bi-directional gate 300, an electric signal (e.g. '$V_{PD}$'—Vphotodiode) representing light that is sensed by LED 308 in the light sensing mode of operation. Light that LED 308 may sense may be in the form of, for example, a series of light pulses that may represent an on command to switch circuit 310 on. Other light-based command patterns or schemes may be used. Decoder 342 (if implemented as a counter) may count the corresponding electric pulses (e.g., an electrical pulse per light pulse) in order to determine whether the series of light pulses is congruent with the on command. If the number of light pulses counted by decoder 342 matches the number of pulses assigned to the on state, decoder 342 outputs a control signal 344 (e.g. "Switch_ctrl") causing switch circuit 310 to transition to the on state. Additional computing may, in some cases, be used to determine if an input light signal indicates a command, or if the light input pattern is more complex than a simple series of pulses.

In the switch's on state, being connected (384) to the voltage supply line, LED driver 320 is powered and, therefore, operational, which means that LED driver 320 may power LED 308 depending on a control signal 322 that may be sent, for example, from a controller identical or similar to controller 160 of FIG. 1. That is, when a device (e.g., an in-vivo device or another device) is switched on by switch circuit 310, LED driver 320 may power LED 308 at times (e.g., according to a predetermined schedule, or during a 'light' time window within the work cycle of the in-vivo device) in order to illuminate, for example, the GI tract. At other times, for example when no illumination is required, LED driver 320 may not power LED 308 even though switch circuit 310 is on.

When switch circuit 310 is in the on state, a LED driving path 390 applies, so control signal 332 (SWITCH_MODE) controlling the conduction state of bi-directional gate 300 is set to a second logic state (e.g., "1") causing bi-directional gate 300 to connect LED driver 320 to LED 308, so LED 308 may be conditionally (depending on control signal 322) activated (illuminate).

As described herein, when a device (e.g., an in-vivo device) using switch 310 is switched on, it may be that LED 308 need not be active. During such 'light' inactive periods, control signal 332 (e.g. SWITCH_MODE) controlling the conduction state (direction) of bi-directional gate 300 is returned to the first logic state (e.g., "0") that causes bi-directional gate 300 to connect LED 308 to LSD 340. If decoder 342 identifies that a light sensed by LED 308 represents an off signal, decoder 342 outputs a control signal 344 (Switch_ctrl) that causes switch circuit 310 to transition to the off state. Being disconnected from the voltage supply +Vbat in the off state of switch circuit 310, LED driver 320 is deactivated (that is, non-operational). Reference numeral 370 is a current source providing electric current (e.g., a few milliamperes) to LED 308.

The following example circuit option is described below for a low-power optical switch based on existing LEDs. As various implementations are available for switch implementation, one embodiment aims for a minimal standby power consumption along with robustness, low area and cost. Thus, an optional optical switch concept is described here for feasibility validation and comparison versus other alternatives. Other circuits may be used.

In some embodiments the LED-based optical switch 304 may utilize one of the in-vivo device LEDs as a light-sensing photodiode when this LED is not used for illumination. In one embodiment the same LED, or set or subset of LEDs, may be used for illumination of the in-vivo environment and, at other times, as an input device(s) to receive control signals. The timing of such functionality is exemplified below in connection with FIG. 5 which shows time periods in which a LED(or LEDs) operates as a light source, and other time periods in which the same LED (or LEDs) is operated as a light sensor.

During a light sensing period, the signal SWITCH_MODE is such that it connects the LED to "ground" and to a detector (comparator, Schmitt trigger, or MOS transistor) which turns to '1'/'0' if the sensed light causes a resulting voltage to cross some threshold (Vth of MOS or Schmitt trigger, or Vref of comparator) and stays at '0'/'0' otherwise.

In some embodiments, additional logic may be used, including a counter—such that the circuit will turn on only after a certain number of light pulses, to avoid accidental switching e.g. due to high ambient illumination. Similarly, the system may turn off after receiving several light pulses (sensed during the operation as exemplified in FIG. 5).

When the LED is in illumination mode, the SWITCH_MODE signal is low, disconnecting the LED from ground and the light detector, and, instead, connecting it to the VLED_COM voltage from the boost DC/DC power supply and the current source in the in-vivo device.

Figure 4:
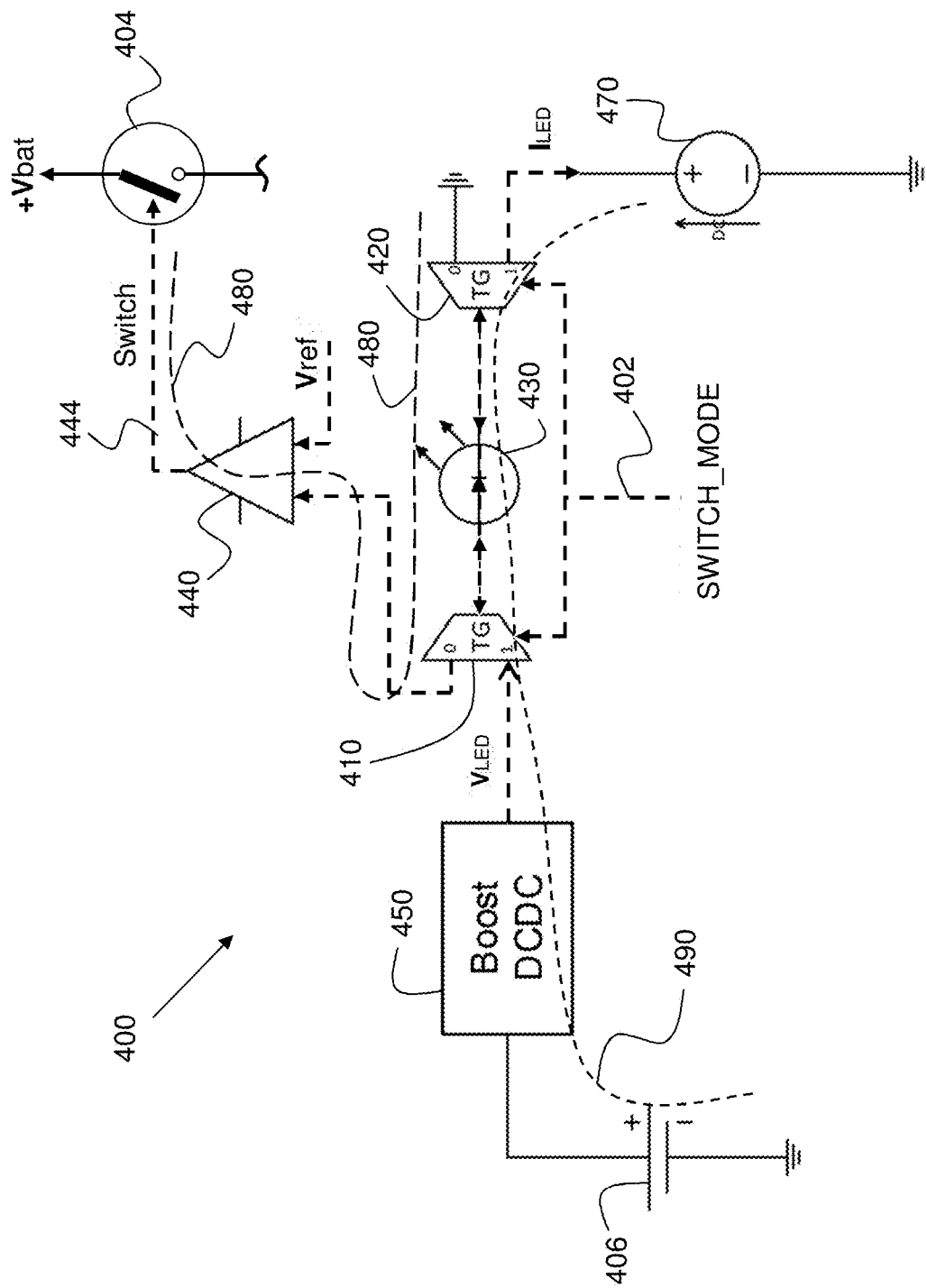
FIG. 4 shows an electrical circuit according to another example embodiment.

FIG. 4 schematically illustrates an optical switch circuit 400 according to another example embodiment. (This embodiment includes two bi-directional gates 410, 420.) While in the embodiment shown in FIG. 3B the "light source"/"light sensing" switching functionality is performed by using one bi-directional gate (300) and a switch (360), in the embodiment shown in FIG. 4 the light source/light sensing switching functionality is performed by using two bi-directional gates (410, 420), that is, the switch (360) of FIG. 3B may be replaced by a bi-directional gate.

Switch circuit 400 includes an on/off switch circuit 404, two bi-directional gates, designates as bi-directional gates 410 and 420, a LED 430, a light signal detector (LSD) 440, and a LED driver 450. Each one of bi-directional gates 410 and 420 may be similar, structurally and/or functionally, to bi-directional gates 230 or to bi-directional gate 300.

When control signal SWITCH_MODE (sown at 402) is at a first logic value (e.g., "0"), bi-directional gates 410 and 420 may enable a conduction path 480 in which LED 430 is, or can be, used as a light sensor while a LED power path 490 may be disabled. When control signal SWITCH_MODE is at a second logic value (e.g., "1"), bi-directional gates 410 and 420 may enable LED power path 490 in which LED is powered by LED driver 450 while conduction path 480 in which LED 430 is, or can be, used as a light sensor may be disabled. Reference numeral 406 is a power source (e.g., battery). Reference numeral 470 is an electrical current source.

If one LED is used for illumination and for sensing light, the light signal transitioning the on/off switch from the off state to the on state may include a series of light pulses that is different than a series of light pulses that is used to transition the on/off switch from the on state to the off state, and the switch control circuit may include a decoder to distinguish between the two series of light pulses. In another example, different light pulses may be used to distinguish between the two states. For example, a 'short' light pulse may represent a command to transition the switch to the on state, while a 'longer' pulse may represent a command to transition the switch to the off state. In another example, a light having a first wavelength may represent a command to transition the switch to the on state, while a light having a second wavelength may represent a command to transition the switch to the on state. Other control signals may be used.

If two or more LEDs are used as light sensor(s), distinguishing between the on and off states may be implemented, for example, by using different LEDs; namely, while certain LEDs may be used to sense a transition to the on state, other or different LEDs may be used to sense a transition to the off state. (Other methods may be used to distinguish between the on and off states of a switch.)

Figure 5:
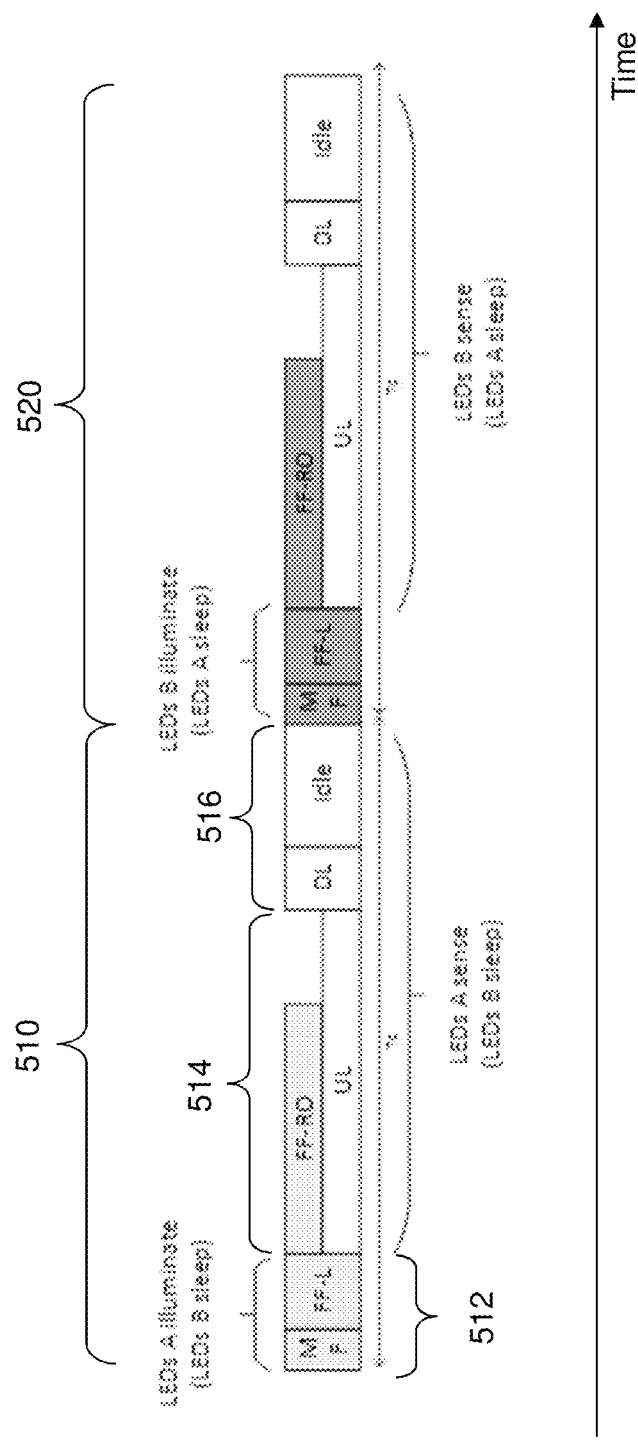
FIG. 5 shows two work cycles of an in-vivo device in accordance with an example embodiment.

FIG. 5 schematically illustrates two example work cycles (510, 520) of an in-vivo device according to an example embodiment. The in-vivo device subject of work cycles 510 and 520 includes two imagers; other numbers of imagers may be used. Work cycle 510 shows activities of a first imager ('A') of the in-vivo device, and work cycle 520 shows activities of a second imager ('B') of the in-vivo device.

During work cycle 510, LEDs B (the LEDs used as the light source for the second imager) are always deactivated; that is, they are neither used for illumination nor as a light source during work cycle 510. During work cycle 520, LEDs A (the LEDs used as the light source for the first imager) are always deactivated; that is, they are neither used for illumination nor as a light source during work cycle 520.

During period 512, LEDs A illuminate and the imager captures an image. During period 514, LEDs A do not illuminate, and the in-vivo device transfers an image frame, for example, to an external receiver/recorder. During period 516, LEDs A do not illuminate and the in-vivo device may receive data (DL) from the external receiver/recorder. Period 516 may also include an idle period during which the in-vivo device may neither capture an image nor transmit data or receive data. Therefore, during periods 514 and 516 LEDs A may be used as light sensors standing by to sense light signal representing an off command to switch the in-vivo device off. Work cycle 520 is analogous to work cycle 520 except that LEDs A of the first imager and LEDs B of the second imager change roles.

A device, system and method in accordance with some embodiments of the invention may be used, for example, in conjunction with a device which may be swallowed. However, the scope of the present invention is not limited in this regard.

Sub-aspects of some individual embodiments may be used with other embodiments. While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A switching circuit comprising:
a switch circuit switchable between an on state which electrically connects a power supply with at least one circuit and an off state which electrically disconnects the power supply from the at least one circuit;
an LED driver configured to power one or more light emitting diodes (LEDs), wherein at least one of the one or more LEDs is used both as a light source and a light sensor;
an LED signal decoder configured to receive an output signal from a light sensor comprising at least one LED selected from the one or more LEDs, and to control an on/off state of the switch circuit based on light sensed by the light sensor; and
a bi-directional gate circuit switchable between a first conducting state in which the bi-directional gate circuit connects the light sensor to the LED signal decoder and a second conducting state in which the bi-directional gate connects the LED driver to the one or more LEDs including the at least one LED selected from the one or more LEDs functioning as the light sensor,
wherein when the switch circuit is in the off state such that the power supply is electrically disconnected from the at least one circuit, the bi-directional gate is in the first conducting state,
wherein when the switch circuit is in the on state such that the power supply is electrically connected with the at least one circuit, the bi-directional gate is switchable between the first conducting state and the second conducting state while the switch circuit remains in the on state.

2. The switching circuit as in claim 1, wherein the bi-directional gate and the LED driver are powered regardless of the on/off state of the switch circuit.

3. The switching circuit as in claim 1, wherein the LED driver is configured to receive an illumination control signal to select LEDs for illumination.

4. The switching circuit as in claim 3, wherein the LED driver is configured to power the selected LEDs according to a predetermined schedule.

5. The switching circuit as in claim 1, wherein the conducting state of the bi-directional gate is configurable by a control signal.

6. The switching circuit as in claim 5, wherein when the switch circuit is in the off state, the control signal is configured to be set to a first logic state causing the bi-directional gate to connect the light sensor to the LED signal decoder, and
wherein when the switch circuit is in the on state, the control signal is configured to be switchable between the first logic state and a second logic state causing the bi-directional gate to connect the LED driver to the one or more LEDs.

7. The switching circuit as in claim 1, wherein the LED driver comprises a DC/DC converter configured to power the one or more LEDs and a current source for each of the one or more LEDs.

8. The switching circuit as in claim 1, wherein the bi-directional gate circuit comprises a multiplexer.

9. The switching circuit as in claim 8, wherein the multiplexer connects the one or more LEDs to the LED driver for illumination or connects the light sensor to the LED signal decoder to sense light.

10. The switching circuit as in claim 8, wherein the multiplexer comprises a sensor LED selector (SLS) to select a subset of the one or more LEDs for operation as the light sensor.

11. The switching circuit as in claim 1, wherein the bi-directional gate circuit comprises a first multiplexer configured to connect a first end of a LED of the one or more light emitting diodes (LEDs) to the power supply or to a light sensing circuit, and a transistor configured to connect a second end of the LED to an electric current source or to a ground potential.

12. An in-vivo device comprising:
one or more light emitting diodes (LEDs);
a power supply;
at least one circuit and an on/off switching circuit, the on/off switching circuit comprising:
a switch circuit switchable between an on state which electrically connects the power supply with the at least one circuit and an off state which electrically disconnects the power supply from the at least one circuit;
an LED driver configured to power the one or more light emitting diodes (LEDs), wherein at least one LED of the one or more LEDs is used both as a light source and a light sensor;
a LED signal decoder configured to receive an output signal from a light sensor comprising at least one LED selected from the one or more LEDs, and to control an on/off state of the switch circuit based on light sensed by the light sensor; and
a bi-directional gate circuit switchable between a first conducting state in which the bi-directional gate circuit connects the light sensor to the LED signal decoder and a second conducting state in which the bi-directional gate connects the LED driver to the one or more LEDs including the at least one LED selected from the one or more LEDs functioning as the light sensor, wherein when the switch circuit is in the off state such that the power supply is electrically disconnected from the at least one circuit, the bi-directional gate is in the first conducting state, wherein when the switch circuit is in the on state such that the power supply is electrically connected with the at least one circuit, the bi-directional gate is switchable between the first conducting state and the second conducting state while the switch circuit remains in the on state.

\* \* \* \* \*